US012685450B1

(12) United States Patent
Niehaus et al.

(10) Patent No.:  US 12,685,450 B1
(45) Date of Patent:       Jul. 21, 2026

(54) ROBUST DETECTION OF A CHANGE IN A PHYSIOLOGICAL METRIC

(71) Applicant: Apple Inc., Cupertino, CA (US)

(72) Inventors: Katherine Niehaus, San Francisco, CA (US); Adeeti V. Ullal, Los Altos, CA (US); William R. Powers, III, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 349 days.

(21) Appl. No.: 18/204,013

(22) Filed: May 31, 2023

Related U.S. Application Data

(60) Provisional application No. 63/349,059, filed on Jun. 4, 2022.

(51) Int. Cl.
*A61B 5/024* (2006.01)
*A61B 5/00* (2006.01)

(52) U.S. Cl.
CPC ............ *A61B 5/024* (2013.01); *A61B 5/7275* (2013.01); *A61B 5/7289* (2013.01)

(58) Field of Classification Search
CPC ...... A61B 5/024; A61B 5/7275; A61B 5/7289
See application file for complete search history.

(56) References Cited

U.S. PATENT DOCUMENTS

2016/0058367 A1* 3/2016 Raghuram ............. A61B 5/681
600/479

* cited by examiner

*Primary Examiner* — Tammie K Marlen
(74) *Attorney, Agent, or Firm* — Brownstein Hyatt Farber Schreck, LLP

(57) ABSTRACT

Embodiments are directed to systems and methods for determining a change in a physiological metric over a target period of time. A plurality of data sets may be used to generate a plurality of contextual signals. Each of these contextual signals may be associated with a different activity context, and may be used to generate a plurality of instances of the physiological metric. Information about the amount of change of each instance of the physiological metric may be used to estimate an overall amount of change in the physiological metric over the target period of time.

10 Claims, 2 Drawing Sheets

ROBUST DETECTION OF A CHANGE IN A PHYSIOLOGICAL METRIC

CROSS-REFERENCE TO RELATED APPLICATION

The application is a nonprovisional and claims the benefit under 35 U.S.C. § 119(e) of U.S. Provisional Patent Application No. 63/349,059, filed Jun. 4, 2022, the contents of which are incorporated herein by reference as if fully disclosed herein.

FIELD

The described embodiments relate generally to systems and methods for monitoring changes in a physiological metric of a target period of time. More specifically, the systems and methods calculate multiple instances of the physiological metric across multiple activity contexts, and use these multiple instances to determine an overall change to the physiological metric.

BACKGROUND

Wearable electronic devices are increasingly incorporating sensing systems that include one or more sensors that measure physiological parameters of a user. These sensors may be able to collect physiological information about a user over longer periods of time such as multiple hours, days, and weeks. This physiological information can be used to calculate physiological metrics that reflect a user's level health or fitness. For example, physiological information collected from a user may be used to estimate $VO_2$ max, which is a metric that represents the maximum volume of oxygen that a user can extract from air the user inhales. While metrics like $VO_2$ max may be representative of a user's cardiopulmonary capacity (i.e., their level of cardio fitness), it may difficult to determine if changes in these metrics over time are indicative of a change in a user's capacity or merely temporary variations resulting from changes in the user's lifestyle or environment. Accordingly, it may be desirable to provide robust detection of changes in a physiological metric.

SUMMARY

Embodiments of the systems and methods described herein are directed toward estimating a change in a physiological metric over time. Some methods include generating a plurality of contextual signals for a plurality of activity contexts, generating a plurality of metric data sets for the plurality of activity contexts, and estimating a change in the physiological metric using the plurality of metric data sets. Each metric data set may include multiple values of the physiological metric calculated using a corresponding contextual signal. In some instances, the methods further include generating a plurality of sets of change metrics for the plurality of activity contexts, where each set of change metrics is generated from a corresponding metric data set. The change metrics may include an estimated rate of change of the multiple values of the physiological metric.

In some embodiments, a system includes a sensor unit having a set of sensors and configured to output a plurality of data sets associated with the target period of time. The system may further include a signal generator configured to generate a plurality of contextual signals using the plurality of data sets, where each contextual signal is associated with a different corresponding activity context. The system may also include a metric generator configured to generate a plurality of metric data sets, wherein each metric data set includes multiple values of the physiological metric calculated using a corresponding contextual signal, as well as a change detection unit configured to generate an estimate of the overall change in the physiological metric over the target period of time using the plurality of metric data sets. In some instances, the system further includes a normalization unit configured to normalize each of the plurality of contextual signals using a corresponding set of factors. The change detection unit may include a metric change unit that generates sets change metrics from the metric data sets and an overall change unit that generates the estimate of the overall change.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1:
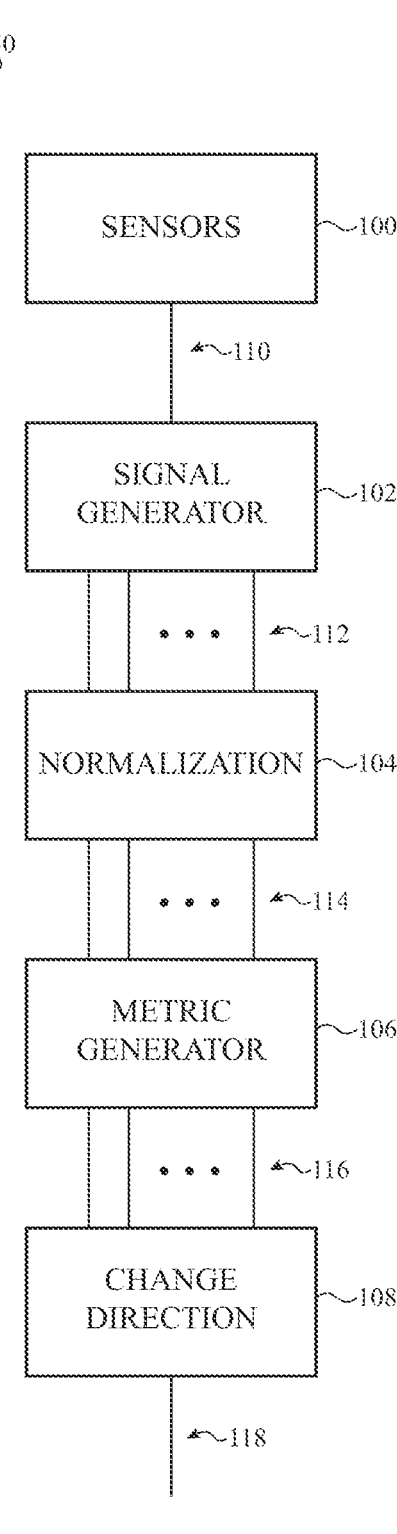
FIG. 1 shows a block diagram of a system can be used to determine a change to a physiological metric as described herein.

It should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Embodiments disclosed herein are systems and methods directed to measuring a change in a physiological metric over a target period of time. To determine this change, a plurality of instances of the physiological metric are calculated over the target period of time, where each instance of the physiological metric is associated with a different activity context. Specifically, each instance of the physiological metric includes multiple values of the physiological metric at different points in the target period of time, and these values are calculated using data associated with the corresponding activity context.

Each instance of the physiological metric may be analyzed to determine a change metric (e.g., a rate of change) representing a change in that metric instance over the target period of time. The systems and methods described herein may thereby generate a plurality of change metrics corresponding to the plurality of different activity contexts. These change metrics may be further analyzed to determine an overall change metric, which represents an overall estimate of how much the physiological metric has changed over the target period of time.

By looking at the physiological metrics across multiple activity contexts, the systems and methods described herein may provide a more robust estimation of a change in the physiological metric. Specifically, this allows the systems and methods described herein to better account for temporary variations that result from confounding factors that may impact an individual measurement of the physiological metric but not represent a meaningful change in the physiological metric over time. For example, depending on the underlying data used to calculate a physiological metric such as a $VO_2$ max estimate, individual estimates may vary at least in part based on a user's recent activity, such as how active they've been earlier that day, how much they slept the night before, what they've had to eat that day, and so on. These variations, however, do not necessarily indicate a change in a user's ability to extract oxygen from inhaled air or their overall cardiopulmonary capacity. The systems and methods described here may account for temporary variations in a calculated physiological metric, and may do so across multiple activity contexts, thereby providing a more robust estimation of a change in the physiological metric over time.

These and other embodiments are discussed below with reference to FIGS. 1 and 2. However, those skilled in the art will readily appreciate that the detailed description given herein with respect to these figures is for explanatory purposes only and should not be construed as limiting.

FIG. 1 shows an example of a system 150 that may be used to calculate a change in a physiological parameter over a target period of time. As shown, the system 150 includes a sensor unit 100, a signal generator 102, a normalization unit 104, a metric generator 106, and a change detection unit 108. The sensor unit 100 includes a plurality of sensors, and the outputs of these sensors may be used to generate a plurality of data sets 110 for the target period of time, each data set associated with a different data type. Example data types include heartbeat data types (e.g., a data type associated with a heartbeat measurement such as heart rate, heart rate variability, resting heart rate) and activity data types (e.g., a data type associated with motion-based measurements such as mechanical work, activity type, or activity intensity), as will be discussed in more detail below.

Multiple data sets 110 collected over the target period of time, each associated with a corresponding data type, are passed to a signal generator 102, which uses these data sets 110 to generate a plurality of contextual signals 112 for a corresponding plurality of activity contexts. Each contextual signal 112 is associated with a different activity context, and includes a data subset for each of one or more data types. Each data subset includes a subset of data points selected from a corresponding data set 110 received by the signal generator 102. Specifically, the data points selected for a given data subset are those that satisfy a set of criteria for the corresponding activity context.

As an example, each activity context may be associated with a different type of activity (e.g., walking, running, cycling). In these instances, the signal generator 102 may output a different contextual signal 112 for each of multiple activity types. Individual data points from some of the data sets 110 may be associated with a given activity (e.g., the data point represents physiological information that was collected while a user was engaged in that activity). As an example, for a given data set 110 or group of data sets 110, the signal generator 102 may use data points associated with a walking activity type to form a first contextual signal, may use data points associated with a running activity type to form a second contextual signal, and so on. In other words, data collected while the user was walking would be used to generate the first contextual signal and data collected while the user was running would be used to generate the second contextual signal.

Each contextual signal will be used to calculate a different instance of the physiological metric, as will be described in more detail below. In some instances, it may be desirable to normalize some or all of contextual signals 112 to help account for variations that may occur in a given data type over time (and may thereby introduce unwanted variations in the calculated instances of the physiologic metric). For example, various factors may impact how a user's heart rate responds to exercise. The user may perform the exact same activity on two separate days, but their heart rate may respond differently in each instance depending on how much they had slept, what they'd had to eat or drink that day, how much they had already exercised in the prior days or hours, if they were ill, and so forth. When this heart rate information is used to estimate a physiological metric such as $VO_2$ max, these variations may cause fluctuations in the calculated estimate that don't reflect (or otherwise obscure) actual changes to the physiological metric itself. In the example of $VO_2$ max, it may be difficult to know if a change in the estimated $VO_2$ max of a user over a time is based on an actual change to the user's $VO_2$ max (and thereby their level of cardio fitness), or is being skewed by these confounding factors that impact the calculated estimates.

To address this, the signal generator 102 may pass the plurality of contextual signals 112 to the normalization unit 104, which normalizes one or more data subsets of the contextual signals 112 based on one or more factors. Specifically, the normalization unit 104 may adjust certain data points in some or all of the data subsets of a given contextual signal 112 to account for a given factor or set of factors. Example factors can include certain heartbeat information (e.g., an average heart rate, a resting heart rate, or a heart rate variability), activity information (e.g., an amount and/or intensity of activity), an amount of sleep calculated, and/or nutrition information (e.g., caloric intake, caffeine intake, types and/or quantify of food eaten) calculated over a time period preceding a data point. The normalization unit 104 may perform multiple normalization operations for each data subset of a given contextual signal 112 to account for multiple factors, such as discussed in more detail below.

The normalization unit 104 may output a plurality of normalized contextual signals 114 to the metric generator 106. The metric generator 106 receives the normalized contextual signals 114 from the normalization unit 104 (or the contextual signals 112 directly from the signal generator 102 in instances where the system 150 does not include a normalization unit 104), and uses the contextual signals to generate a plurality of metric data sets 116 corresponding to the plurality of activity contexts. Each metric data set 116 is associated with a different corresponding activity context, and is generated using the contextual signal (e.g., contextual signal 112 or normalized contextual signal 114) for that activity context. Said another way, metric generator 106 will generate a metric data set 116 for each contextual signal it receives, though it should be appreciated that in some instances the metric generator 106 will only generate a metric data set 116 for those contextual signals that meet a set of criteria (e.g., a corresponding minimum number of data points for each data subset of the contextual signal).

Each metric data set 116 represents a different instance of a physiological metric as discussed above, and includes multiple values of the physiological metric calculated from the corresponding contextual signal. As a result, each activity context will have a metric data set 116 with multiple values of the physiological metric in the target period of time. In the example above where each activity context is associated with a different type of activity, a first metric data set may include values of a physiological metric calculated using data when a user was walking during the target period of time, a second metric data set may include values of a physiological metric calculated using data when a user was running during the target period of time, and so on.

The plurality of metric data sets 116 may be provided to the change detection unit 108, which may use these metric data sets 116 to estimate an overall rate of change for the physiological metric over the target period of time. The detection unit 108 may provide an output 118 that includes a set of overall change metrics (e.g., an estimated overall rate of change for the physiological metric over the target period of time, a confidence value associated with the estimated rate of change, or the like). The set of overall change metrics may be used by the system 150 to alter operation of one or more devices associated with the system. For example, if the estimated overall rate of change over the target period of time is above a certain threshold, the system 150 may notify a user to alert the user to this change. Additionally or alternatively, these changes may be used by the system in generating coaching prompts and/or recommendations for user actions.

Figure 2:
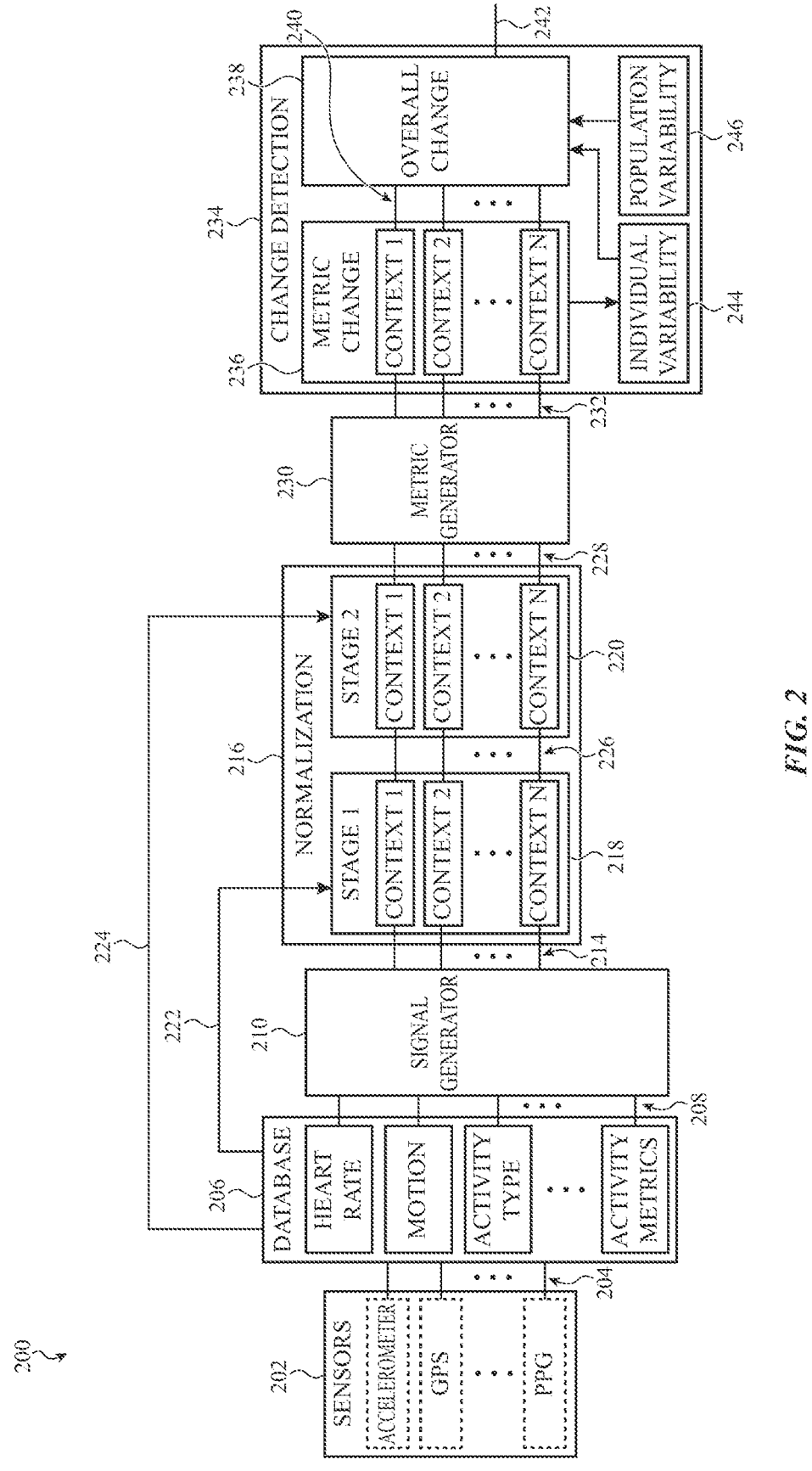
FIG. 2 shows an example system that can be to determine a change to a physiological metric as described herein.

FIG. 2 depicts an example of a system 200 that may utilize the various components of system 150 of FIG. 1. As shown there, the system 200 includes a set of sensors 202 which provide a corresponding set of sensor measurements 204 to a database 206 (which may collectively form the sensor unit 100 of system 150). The set of sensors 202 includes at least those sensors that provide any measurements that are necessary to generate the contextual signals and resulting metric data sets discussed above. While the set of sensors 202 shown in FIG. 2 includes an accelerometer, a GPS, and a photoplethysmography (PPG) sensor, these are illustrative examples and it should be appreciated that the set of sensors 202 may include a wide variety of sensors. Example sensors include, but are not limited to, inertial sensors (e.g., accelerometers, gyroscopes, and magnetometers), environmental sensors (e.g., pressure sensors and temperature sensors), physiological sensors (e.g., PPG sensors, pulse oximeters, electrocardiogram sensors, electromyography sensors, electroencephalography sensors, and skin- or body-temperature sensors), location tracking sensors (e.g., GPS), combinations thereof, or the like.

The set of sensor measurements 204 generated by the set of sensors 202 may be used to generate the underlying data points for a variety of data types, and these data points may be stored in the database 206 (which generally represents the overall collection of data that will be used to generate the contextual signals and metric data sets, but does not require this data be stored in any particular location or locations). For example, measurements from a PPG sensor and/or an electrocardiogram sensor may be used to calculate one or more data types associated with a user's heartbeat. In these instances, one data type may be a heart rate data type, in which individual data points relate to the number of heartbeats that are detected over a time interval. Another data type may be a heart rate variability data type, in which individual data points relate to a variation in the time interval between heartbeats as calculated over a time interval. Still another data type may be a resting heart rate data type, in which individual data points relate to a heart rate value derived from measurements taken while a user is in a resting state.

It should also be appreciated that different data types may include the same parameter, but calculated over a different time interval. In these instances, the same underlying sensor measurements may be used to generate the data for these data types, but the different time intervals may result in different data. For example, one heart rate data type may include heart rate measurements calculated over a first time interval (e.g., two minutes) and another heart rate data type may include heart rate measurements calculated over a second time interval (e.g., two hours). The data types may be used for different purposes (e.g., one may be used to generate a contextual signal and the other is used as an input for a normalization operation).

The database 206 may include any suitable combination of data types that may be used in estimating the overall change in the physiological metric, and thus the selection of data types may depend on the underlying physiological metric being calculated. For example, some physiological metrics (such as $VO_2$ max estimates) may require one or more heart rate data types (and/or other heartbeat data types as discussed above) and one or more activity data types. Activity data types provide information relating to a user's motion during certain time intervals, and can include an activity type data type (e.g., a categorization of a given period of time as associated with a type of activity, such as walking, running, cycling, or the like), an activity metric data type (e.g., a characterization of the activity during a time interval, such as the overall amount of an activity or an intensity level of the activity during a time interval), or a motion metric data type (e.g., a characterization of gross user motion, such as mechanical work, during a time interval). Examples of other data types include nutrition data types (e.g., caloric, alcohol, or caffeine intake over a time interval), sleep data types (e.g., sleep quality or sleep duration during a time interval), and user population information (e.g., a user's age or geographic location). It should be appreciated that while data points for some data types are calculated using one or more sets of the sensor measurements 204, some data types may additionally or alternatively include data points that are manually entered by a user.

To calculate a change in the physiological metric over the target period of time (e.g., over a number of days, weeks, or months), data from the database 206 may be used to generate a plurality of data sets 208 (each corresponding to a different data type) associated with the target period of time. Specifically, for a plurality of data types (e.g., a heart rate data type, a motion metric data type, an activity type data type, and an activity metric data type are shown as an illustrative example in FIG. 2), data points of each of these data types that correspond to the target period of time are collected to form a corresponding data set 208 for the corresponding data type.

A signal generator 210 receives the plurality of data sets 208 as inputs, and uses the plurality of data sets 208 to generate a plurality of contextual signals 214 as described above. Specifically, the signal generator 210 generates a contextual signal 214 for each of a plurality of activity contexts. In FIG. 2, contextual signals 214 are generated for N different activity contexts, which may represent any suitable number of activity contexts, such as two, three, four, or five or more activity contexts. As mentioned above, in some variations each activity context is associated with a different type of activity, and thus the activity type data type is used to determine which data points of a given data point will be associated with a given contextual signal 214. In other variations, each activity context is associated with a different combination of a type of activity (as defined by an activity type data type) and an intensity of activity (as defined by an activity metric data point) for that type of activity. For example, one activity context may be walking at a first speed range and another activity context may be walking at a second speed range. In these instances, data points collected while a user was walking at a pace in the first speed range would be used to generate a first contextual signal, and data points collected while the user was walking at a pace in the second speed range would be used to generate a second contextual signal.

To generate a contextual signal 228 for a given activity context, a subset of the corresponding data set for each of one or more data types is selected. For example, in one variation, the contextual signals 228 are each generated from a subset of the data set for a heart rate data type and a subset of the data set for a motion metric data type. In this variation, each contextual signal 228 would include two data subsets, one for the heart rate data type and one for the motion metric data type. It should be appreciated that the signal generator 210 need not use every data point that corresponds to a given activity context in the target period of time when generating the contextual signal 228 for that activity context. The signal generator 210 may apply inclusion criteria to potential data points before including it in a given contextual signal 228. For example, the signal generator 210 may require a minimum number of candidate data points in a particular time interval (e.g., five minutes) to add those data points to a given contextual signal 228. In some instances, there may be a certain amount of data that is needed to calculate an instance of the physiological metric, and the inclusion criteria may ensure that data points added to a given contextual signal is usable to calculate one or more values of an instance of the physiological metric.

Similarly, the number of contextual signals 214 generated by the signal generator 210 is dependent on the nature of the data corresponding to the target period of time. For example, in instances where each activity context corresponds to a different type of activity, the number of contextual signals 214 may depend on how many activity types are present in the activity type data type during the target period of time. While the system may be capable of tracking several user activities (e.g., running, walking, cycling, swimming, rowing, high intensity interval training, etc.), a particular user may have only engaged in a subset of these activities during the target period of time and the signal generator 210 may only be able to generate contextual signals for the subset of activities. The systems described herein may have a minimum set of output requirements from the signal generator 210 (e.g., a minimum number of contextual signals, each having a minimum amount of data), and some variations of the systems described herein may be able to accommodate additional outputs beyond the minimum requirements.

The contextual signals 214 may be passed from the signal generator 210 to a normalization unit 216, which may normalize the contextual signals based on one or more factors. Each contextual signal 214 may undergo one or more normalization operations, each utilizing a different set of factors. For example, the normalization unit 216 shown in FIG. 2 includes a first stage 218 and a second stage 220, though it should be appreciated that the normalization unit

216 may alternatively include a single stage or three or more stages. At each stage, one or more of the data subsets is normalized using a corresponding factor. For example, in instances where a contextual signal includes a first data subset for a heart rate data type and a second data subset for a motion metric data point, a given stage may include normalizing the first data subset using a first factor and normalizing the second data subset using a second factor. When there are multiple data subsets in a contextual signal, different data subsets may undergo different numbers of normalization operations.

The normalization unit 216 may receive or derive its factors from data received from the database 206. For example, as shown in FIG. 2, the first stage 218 receives a first set of data 222 from the database 206 while the second stage 220 receives a second set of data 224 from the database 206. For example, the first stage may receive data from a data type associated with heartbeat information (e.g., heart rate, resting heart rate, or heart rate variability). For each data point (or set of data points) in a data subset of a given contextual signal, the first stage may use this data to calculate a value of a normalization factor (e.g., an average heart rate in the 24 hours preceding the data point), and then use this value of the normalization factor to adjust the value of that data point (or set of data points). Each contextual signal is separately normalized, and thus the amount of normalization that occurs for a given factor may vary between different activity contexts (as some activity contexts are more susceptible to variations from confounding factors). Additionally, in some instances population information of a user may be used to adjust the normalization provided by the normalization unit. Different populations may respond differently to the same change in a normalization factor (e.g., a change in the amount of sleep may impact the heart rate of users in one age group more than it impacts the heart rate of users in a different age group), and thus it may be desirable to alter the strength of the normalization based on the user's population information.

The first stage 218 of the normalization unit 216 produces a first plurality of normalized contextual signals 226 (based on a first set of factors), while the second stage 220 produces a second plurality of normalized contextual signals 228 (based on a second set of factors). These normalized contextual signals 228 may then be passed to a metric generator 230. The metric generator 230 in turn produces a plurality of metric data sets 232, one for each contextual signal 214 and its associated activity context. To generate each metric data set 232, the data subset or subsets from the corresponding contextual signal 214 is analyzed to calculate a set of values of the physiological metric, which collectively form the metric data set 232. Each value of the physiological metric is associated with a different point in time within the target time period. For example, in some variations where the physiological metric is an estimation of $VO_2$ max, this estimation may be determined using a user's heart rate and movement information over different time intervals. In these instances, each activity context (and its associated metric data set 232) will include a set of $VO_2$ max estimates calculated at a corresponding set of times in the target time period.

The plurality of metric data sets 232 are passed from the metric generator 230 to a change detection unit 234. As shown in FIG. 2, the change detection unit 234 may include a metric change unit 236 and an overall change unit 238. The metric change unit 236 receives the different instances of the calculated metric (i.e., the plurality of metric data sets 232) and calculates a plurality of sets of change metrics 240, one set for each metric data set 232. Each set of change metrics 240 can include one or more change metrics associated with the corresponding instance of the physiological metric (e.g., an estimated rate of change for the physiological metric over the target period of time for that activity context, a confidence value associated with the estimated rate of change, a measurement of the variability of the physiological metric over the target period of time, or the like).

The overall change unit 238 may receive the plurality of the set of change metrics 240 from the metric change unit 236, and determines a set of overall change metrics 242 (e.g., an estimated overall rate of change for the physiological metric over the target period of time, a confidence value associated with the estimated rate of change, or the like). For example, in some variations, the overall change unit 238 may provide a set of overall change metrics 242 that includes an estimated overall rate of change for the physiological metric over the target period of time, as well as a confidence value associated with the estimated overall rate of change. In some instances, the overall change unit 238 may utilize a statistical model that uses the plurality of sets of change metrics 242 of the metric change unit 236 to calculate the overall rate of change.

The overall change unit 238 may receive and use additional information regarding the different activity contexts that may impact the output of the overall change unit 238. For example, the overall change unit 238 may receive information about the quantity or quality of the metric data sets used to calculate the change metrics. In these instances, the overall change unit 238 may receive one or more additional metrics that reflect the number of values of the calculated physiological metric in a metric data set, how those values were distributed over the target period of time, and/or the quality of the individual values of the calculated physiological metric in the metric data set. As an illustrate example, if the target period of time spans a month or longer, the overall change unit 238 may assign less weight to change metrics for an activity context that was only observed over a few days than it would for change metrics for a different activity context that was observed over multiple weeks. It should be appreciated that in some instances, these differences may be accounted for using a confidence value that is outputted along with the other change metrics.

In some instances, the overall change unit 238 may receive as additional inputs an expected variability for the metric data set 232 associated with each activity context. For example, in the variation shown in FIG. 2, the change detection unit 234 includes an individual variability module 244 that generates a user-specific value of the expected variability for each of the metric data sets 232 and its corresponding activity context. The change detection unit 234 may receive information about the variability of the individual activity contexts (and may collect this information over different target time periods) to generate these user-specific values.

This may allow the overall change unit 238 to account for different levels of variabilities across activity contexts. For example, estimates of a physiological metric calculated for a first activity context associated with a particular user while running may exhibit larger variability over time than estimates calculated for a second activity context associated with that particular user while walking. In these instances, the overall change unit 238 may assign more weight to the change metrics calculated from the first activity context as compared to the change metrics calculated from the second activity context.

Additionally or alternatively, the change detection unit 234 may include a population variability module 246 that provides population-based values of the expected variability for each of the metric data sets 232 and its corresponding activity context. In addition to user-specific variability, some activity contexts are generally expected to have more variability than others for certain segments of the general population. This information can also be used to adjust the weight assigned to the various inputs to the overall change unit 238. In these variations, the specific population-based values provided by the population variability module 246 to the overall change unit 238 will be selected based on the user's population information (e.g., to make sure that the population information provided by population variability module 246 reflects the user). Overall, the inputs to the overall change unit 238 may be used to provide a robust estimation of a change in a physiological metric that may account for both user-specific and population-specific variations that may occur in the underlying data.

In general, the systems described above may be implemented by at least one electronic device, which in some instances may include multiple devices. The electronic device may include one or more processing units, an input/output mechanism (e.g., an input/output device, input/output port, or a button, a haptic output interface, or the combination thereof), a display (e.g., a light-emitting display), a memory or a storage device, and a power supply. The electronic device may further include one or more sensors of the sensor units described above. It should be appreciated that the sensor units described herein may include sensors distributed across multiple different electronic devices (e.g., wearable devices such as smart watches, bands, rings, or the like), and thus the system may collect measurements from sensors of multiple devices.

The one or more processing units can communicate, either directly or indirectly, with some or all of the components of the system, and may be configured to perform the operations performed by the various components of FIGS. 1 and 2 (e.g., the signal generator 102, the normalization unit 104, and so on). For example, a system bus or other communication mechanisms can provide communication between the one or more processing units, the power supply, the memory, the one or more sensors, the input/output mechanism, and the display. The one or more processing units may be implemented as any electronic device capable of processing, receiving, or transmitting data or instructions. By way of a non-limiting example, the one or more processing units may be a microcontroller, a microprocessor, a central processing unit, an application-specific integrated circuit, an integrated circuit, a field-programmable gate array, a digital signal processor, and/or a system-on-chip (SoC), and so on. Accordingly, the term "processing unit" and similar terms and phrases is meant to encompass a single processor or processing unit, multiple processors, multiple processing units, or other suitably configured computing element or elements.

In some embodiments, various components of the electronic device may be controlled by multiple processing units. For example, select components of the electronic device (e.g., a sensor) may be controlled by a first processing unit, and other components of the electronic device (e.g., the display) may be controlled by a second processing unit, where the first and second processing units may or may not be in communication with each other Accordingly, the various components of FIGS. 1 and 2 may be implemented by a single processing unit or may be distributed across multiple processing units.

In some embodiments, the power supply may be implemented with any device capable of providing energy to the electronic device. For example, the power supply may be one or more batteries or rechargeable batteries. By way of a non-limiting example, the power supply may be a power connector or power cord that connects the electronic device to another power source, such as a wall outlet. In some embodiments, by way of a non-limiting example, the power supply may be implemented as a USB-powered power supply.

In some embodiments, the memory may store electronic data that may be used by the electronic device. For example, the memory may store electrical data or content such as, for example, software instructions, algorithms, audio and video files, documents and applications, device settings and user preferences, timing signals, control signals, and data structures or databases. The memory may be configured as any type of memory. By way of a non-limiting example, the memory may be implemented as random access memory, read-only memory, static random-access memory, Flash memory, removable memory, and/or a hard disk, and so on.

In some embodiments, the I/O mechanism may transmit and/or receive data from a user or another electronic device. An I/O device may include a display, a touch sensing input surface, one or more buttons (e.g., a graphical user interface "home" button, a physical button such as a tact switch button), one or more cameras, one or more microphones or speakers, one or more ports such as a microphone port, and/or a keyboard. In some embodiments, by way of a non-limiting example, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections. An I/O device can also be a software-defined electromechanical button including a sensor to sense user input force, a haptic engine to generate tactile feedback to the user, and a digital circuit to generate button signals for other sub-blocks in the electronic device according to some embodiments, as described herein.

As described above, one aspect of the present technology is measuring data from a sensor unit to calculate a change in a physiological metric. The present disclosure contemplates that in some instances this gathered data may include personal information data that uniquely identifies or can be used to contact or locate a specific person. Such personal information data can include demographic data, location-based data, telephone numbers, email addresses, Twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining the privacy and security of personal information data. Such policies should be easily accessible by users and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and revised to adhere to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A system for estimating an overall change in a physiological metric over a target period of time, the system comprising:

a sensor unit comprising a set of sensors and configured to output a plurality of data sets associated with the target period of time;

a signal generator configured to generate a plurality of contextual signals using the plurality of data sets, wherein each contextual signal of the plurality of contextual signals is associated with a different corresponding activity context of a plurality of activity contexts;

a metric generator configured to generate a plurality of metric data sets, wherein each metric data set includes multiple values of the physiological metric calculated using a corresponding contextual signal of the plurality of contextual signals; and a change detection unit configured to generate an estimate of the overall change in the physiological metric over the target period of time using the plurality of metric data sets.

2. The system of claim 1, wherein each contextual signal comprises a corresponding first data subset selected from a first data set of the plurality of data sets.

3. The system of claim 2, wherein the first data set includes data values of a heart rate data type.

4. The system of claim 2, wherein each contextual signal comprises a corresponding second data subset selected from a second data set of the plurality of data sets.

5. The system of claim 4, wherein the second data set includes data values of a motion metric data point.

6. The system of claim 1, further comprising a normalization unit configured to normalize each of the plurality of contextual signals using a corresponding set of factors, wherein the metric generator receives the plurality of contextual signals after they have been normalized by the normalization unit.

7. The system of claim 6, wherein the normalization unit includes a plurality of stages, each of which is configured to perform a different normalization operation on each of the plurality of contextual signals.

8. The system of claim 1, wherein the change detection unit comprises a metric change unit configured to generate a plurality of sets of change metrics using the plurality of metric data sets, wherein each set of change metrics is associated with a different corresponding activity context of the plurality of activity contexts.

9. The system of claim 8, wherein each set of change metrics of the plurality of sets of change metrics comprises an estimated rate of change of the multiple values of the physiological metric of the corresponding activity context.

10. The system of claim 8, wherein the change detection unit further comprises a overall change unit configured to generate the estimate of the overall change of the physiological metric over the target period of time using the plurality sets of change metrics.

* * * * *